United States Patent [19]

O'Brien et al.

[11] 4,247,693

[45] Jan. 27, 1981

[54] PROCESS FOR PREPARING 2,4,5,6-TETRAAMINOPYRIMIDINE SULFATE

[75] Inventors: Patrick F. O'Brien, Piscataway; John Kazan, Bridgewater; John R. Andrade, Bound Brook, all of N.J.

[73] Assignee: American Cyanamid Company, Stamford, Conn.

[21] Appl. No.: 79,664

[22] Filed: Sep. 28, 1979

[51] Int. Cl.³ .......................................... C07D 239/50
[52] U.S. Cl. .................................................. 544/323
[58] Field of Search ........................................ 544/323

[56] References Cited

U.S. PATENT DOCUMENTS

| | | | |
|---|---|---|---|
| 2,473,802 | 6/1949 | Kuh et al. | 544/320 |
| 3,111,521 | 11/1963 | Hoefle et al. | 544/323 |
| 4,003,699 | 1/1977 | Rose et al. | 544/323 |
| 4,167,633 | 9/1979 | Morrow | 544/323 |

FOREIGN PATENT DOCUMENTS 7712155  1/1979  Netherlands .

OTHER PUBLICATIONS

"J. Chem. Soc." (1953), p. 3721.
"J. Amer. Chem. Soc.", vol. 69, 1947, p. 1814.
"J. Amer. Chem. Soc.", vol. 55, 1933, p. 1667.
"Berichte", vol. 37, 1904, p. 4544.

*Primary Examiner*—Donald G. Daus
*Assistant Examiner*—James H. Turnipseed
*Attorney, Agent, or Firm*—Jack W. Richards

[57] ABSTRACT

A process for preparing 2,4,5,6-tetraaminopyrimidine sulfate is disclosed. The process comprises: (1) reacting about one molecular proportion of 5-nitroso-2,4,6-triaminopyrimidine (NTAP) in water with about 2.0 to 2.5 molecular proportions of zinc dust and about 4.0 to 4.7 molecular proportions of a suitable acid, to provide a reaction mixture having a pH below 7; (2) reacting the reaction mixture at a temperature of about 20° to 65° C. to form the acid salt of 2,4,5,6-tetraaminopyrimidine; (3) adjusting the pH to about 2.0 to 2.5 by adding the suitable acid to form a solution of the acid salt; (4) separating the insoluble materials from step (3) to obtain a wet cake and a mother liquor; (5) adding sulfuric acid to the mother liquor to adjust the pH to about 0.2 to 0.5 while maintaining the temperature at about 20° to 60° C.; (6) cooling the reaction mixture of step (5) to about 0° to 10° C. to precipitate 2,4,5,6-tetraaminopyrimidine sulfate; and (7) recovering the precipitate.

7 Claims, No Drawings

PROCESS FOR PREPARING 2,4,5,6-TETRAAMINOPYRIMIDINE SULFATE

BACKGROUND AND SUMMARY OF THE INVENTION

The present invention relates to a process for preparing 2,4,5,6-tetraaminopyrimidine sulfate. More particularly, it relates to a process for preparing 2,4,5,6-tetraaminopyrimidine sulfate, represented by formula (I), by reducing 5-nitroso-2,4,6-triaminopyrimidine, represented by formula (II), with zinc in the presence of a suitable acid to the corresponding acid salt of 2,4,5,6-tetraaminopyrimidine, and converting the latter to the sulfate salt. The product (I) is useful as an intermediate in the synthesis of methotrexate, an antineoplastic agent for treating cancer in humans.

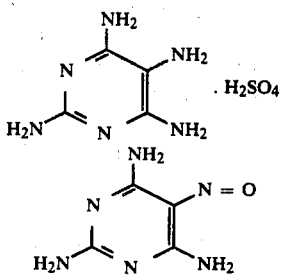

The reduction of 5-nitroso-2,4,6-triaminopyrimidine, hereafter referred to as NTAP, with sodium dithionite and treatment of the resulting 2,4,5,6-tetraaminopyrimidine with sulfuric acid, to form the desired compound of formula (I), hereafter referred to as TAPS, is well known in the art. See, e.g., J. Chem. Soc., 3721 (1953), discussed more fully below. However, the use of sodium dithionite results in the formation of undesirable sulfamate impurities which cannot be easily removed by conventional methods such as reslurrying or recrystallization. The level of impurity may be as high as 40-area percent, as determined by high-pressure liquid chromatography. There is a need, therefore, for a process for the reduction of NTAP to give a reaction mixture which upon acidification with sulfuric acid will give TAPS in high yields and without the sulfamate impurity.

The Applicants are not aware of any prior art publication which, in their respective judgment as a person skilled in the art of preparing 2,4,5,6-tetraaminopyrimidine sulfate, anticipates or renders obvious the process of this invention. However, to fully develop the background of this invention and to establish the state of the requisite art, the following publications are set forth:

U.S. Pat. No. 2,473,802 discloses the preparation of 2,4,5-triamino-6-hydroxypyrimidine by the reduction of 2,4-diamino-5-nitroso-6-hydroxypyrimidine with a mixture of zinc dust and ammonium hydroxide;

Netherlands Patent Application No. 7,712,155, published Jan. 23, 1979, discloses the preparation of 2,4,5,6-tetraaminopyrimidine by the reduction of 5-nitroso-2,4,6-triaminopyrimidine with Raney nickel, or with a nickel salt and sodium borohydride, in an aqueous suspension;

J. Chem. Soc., 3721 (1953), discloses the reduction of several 5-nitrosopyrimidines using sodium dithionite, and the precipitation of the product as an insoluble sulfate salt. Among the compounds prepared in this manner are 6-hydroxy-2,4,5-triaminopyrimidine sulfate and 4,5-diamino-2,6-dihydroxypyrimidine sulfate;

J.A.C.S. 69, 1814 (1947), discloses the preparation of 2,4,5,6-tetraaminopyrimidine bisulfite by reacting 5-nitroso-2,4,6-triaminopyrimidine with sodium dithionite in water at a temperature of about 60°–70° C. The yield of the product obtained was 54% of theoretical;

J.A.C.S. 55, 1667 (1933), discloses the use of sodium dithionite to reduce the 5-nitroso-6-aminouracil to 5,6-diaminouracil. The 5,6-diaminouracil is then isolated as the sulfate salt; and Berichte 37, 4544 (1904), discloses the preparation of 2,4,5,6-tetraaminopyrimidine sulfate by the reduction of 5-nitroso-2,4,6-triaminopyrimidine with ammonium sulfide.

The process of the present invention has the following advantages:

1. The real yield is increased to about 82.5–88.5% versus less than 75% for the dithionite process.
2. The purity of the product is increased to about 99.5% versus about 60–90% for the product of the dithionite process.
3. Productivity is increased about 30% over the dithionite process because the reduction can be carried out at higher concentrations.
4. The need for careful temperature control and pH control is eliminated.
5. The zinc reducing agent is noncorrosive and is easily removed from the effluent liquors thus avoiding discharging of zinc in the effluent.
6. The discharge of sulfurous by-product emissions from dithionite in the reactor and effluent is avoided.

In accordance with the present invention, a process for preparing 2,4,5,6-tetraaminopyrimidine sulfate (TAPS) comprises (1) reacting about one molecular proportion of 5-nitroso-2,4,6-triaminopyrimidine (NTAP) in water with about 2.0 to 2.5 molecular proportions of zinc dust and about 4.0 to 4.7 molecular proportions of a suitable acid, to provide a reaction mixture having a pH below 7; (2) reacting the reaction mixture at a temperature of about 20° to 65° C. to form the acid salt of 2,4,5,6-tetraaminopyrimidine; (3) adjusting the pH to about 2.0 to 2.5 by adding the suitable acid to form a solution of the acid salt; (4) separating the insoluble materials from step (3) to obtain a wet cake and a mother liquor; (5) adding sulfuric acid to the mother liquor to adjust the pH to about 0.2 to 0.5 while maintaining the temperature at about 20° to 60° C.; (6) cooling the reaction mixture of step (5) to about 0° to 10° C. to precipitate 2,4,5,6-tetraaminopyrimidine sulfate; and (7) recovering the precipitate.

In one embodiment, in step (1) the zinc dust is added to provide an initial mixture having a pH of about 8 to 10 and then the suitable acid is added at a rate to provide a temperature rise of about 1° C. per minute and a final pH of about 5 to 6. In a preferred embodiment, in step (1) about 2.1 to 2.2 molecular proportion of zinc dust are added and then about 4.1 to 4.2 molecular proportions of hydrochloric acid are added, to provide a final temperature of about 50° to 65° C. and a final pH of about 5.5 to 5.7; in step (3) the pH is adjusted to about 2.2 to 2.4; and in step (5) about 15–20% by weight of sulfuric acid is added to adjust the pH to about 0.2 to 0.5 while maintaining the temperature at about 40° to 45° C. In a most preferred embodiment, the hydrochloric acid is a mixture of one part by volume of concentrated hydrochloric acid and one part by volume of water.

In another embodiment, in step (1) the zinc dust and acid are added concurrently at a rate to provide a temperature rise of about 1° C. per minute and a final pH of about 5 to 6. In a preferred embodiment, in step (1) about 2.1 to 2.2 molecular proportions of zinc dust and about 4.1 to 4.2 molecular proportions of hydrochloric acid per molecular proportion of 5-nitroso-2,4,6-triaminopyrimidine are added concurrently at a rate to provide a final temperature of about 50° to 65° C. and a final pH of about 5.5 to 5.7; in step (3) the pH is adjusted to about 2.2 to 2.4; and in step (5) about 15-20% by weight of sulfuric acid is added to adjust the pH to about 0.2 to 0.5 while maintaining the temperature at about 40° to 45° C. In a most preferred embodiment, the hydrochloric acid is a mixture of one part by volume of concentrated hydrochloric acid and one part by volume of water.

In yet another embodiment, the acid is selected from the group consisting of hydrochloric acid, hydrobromic acid, sulfuric acid, phosphoric acid, formic acid, acetic acid, and mixtures thereof.

DETAILED DESCRIPTION OF THE INVENTION

The process of the present invention is carried out by reacting a slurry of NTAP in water with zinc dust and an acid to produce a water-soluble salt of 2,4,5,6-tetraaminopyrimidine which is converted by a subsequent reaction with sulfuric acid to TAPS. In carrying out the process, the NTAP is added to a suitable reactor together with about 10-20, preferably about 11-12, parts by weight of water per part by weight of "as is" NTAP charged. The "as is" NTAP used is about 86-92% real NTAP. The NTAP is then reacted with 2.0-2.5, preferably 2.1-2.2, molecular proportions of zinc dust and about 4.0-4.7, preferably about 4.1-4.2, equivalent proportions of a suitable acid per molecular proportion of NTAP charged. The reaction mixture at the start of the reduction has a temperature of about 10°-50° C., preferably about 15°-25° C., and a pH of about 3-10, preferably about 8-10. The reaction mixture is agitated while the acid, or optionally the acid and zinc dust, is added at a rate to provide a temperature of about 20°-65° C., preferably about 60°-65° C., and a reaction mixture having a pH below 7, preferably about 5-6, after the addition of the acid, or the acid and zinc dust, is completed. The time of addition will vary with the temperature of the reaction mixture employed, shorter addition times being used with higher temperatures.

Examples of suitable acids which may be used include the following:
hydrochloric acid,
hydrobromic acid,
sulfuric acid,
phosphoric acid,
formic acid, and
acetic acid,
and the like, or mixtures thereof.

The preferred acid is a mixture of equal parts by volume of water and concentrated hydrochloric acid.

After the addition of the acid is completed in step (1), the pH of the reaction mixture is adjusted to about 2.0-2.5, preferably about 2.2-2.4, by adding additional acid while maintaining the temperature at about 50°-65° C., preferably about 60°-65° C. Optionally, the reaction mixture from step (1) is stirred at about 50°-65° C. for about 20-30 minutes before adjusting the pH to about 2.0-2.5.

A decolorizing agent and a filter-aid are then added to the reaction mixture. The decolorizing agent is added in an amount of about 0.01-0.4 part by weight, preferably about 0.09 part by weight, per part by weight of NTAP used. The filter-aid is added in an amount of about 0.06-0.66 part by weight, preferably about 0.18 part by weight, per part by weight of NTAP.

Suitable decolorizing agents include Darco Decolorizing Carbon G-60 (Atlas Chemical Industries, Inc.), Carbon RB, and the like.

Suitable filter-aids include diatomaceous earths such as Hyflo ® Super-Cel (Johns-Manville Corp.) and the like.

The reaction mixture is then stirred for about 5-30 minutes at above 55° C., preferably at about 60°-70° C. for about 10-20 minutes, and filtered. The resulting filter cake is then washed with about 1-5 parts by weight of water at about 30°-70° C., preferably about one part by weight of water at about 60°-70° C., per part by weight of nitroso compound used.

The filtrate plus the wash liquor is then cooled to about 2°-60° C., preferably about 40°-45° C., and the pH of the combined solution is adjusted to about 0-0.5, preferably about 0.2-0.5, by adding sulfuric acid, preferably about 16-20% by weight sulfuric acid, in at least a stoichiometric amount, preferably about 70-80 mole percent excess above the stoichiometric amount, to form TAPS. Optionally, the reaction mixture is stirred for about 15-30 minutes after the addition of the sulfuric acid is completed.

The reaction mixture is then cooled to about 0°-10° C., preferably to about 5°-10° C., and the resulting precipitate is recovered by conventional means. The wet cake is then rinsed with water at about 5°-10° C. and dried at about 60°-65° C. in a vacuum oven to obtain TAPS in a real yield of about 82-88% of theoretical based on unhydrated TAPS. The product obtained is at least 99.5% by weight TAPS, on an anhydrous basis.

In the preferred embodiment, in step (1) all of the zinc dust is charged to the reactor with the water and NTAP to provide an initial slurry having a pH of about 8-10, more preferably about 9-10, before the acid is added thereto.

In an optional embodiment, the initial mixture of water and NTAP has a pH of about 3-4, preferably about 3.5-3.7, and the zinc dust and hydrochloric acid are added concurrently to provide a temperature rise of about 1° C. per minute and a pH of about 5-6, preferably about 50°-65° C. and a pH of about 5.5-5.7, after the additions of both are completed.

In the process of this invention, the raw effluent obtained in the isolation of TAPS is treated with 50% caustic soda to adjust the pH to about 7-9 to precipitate zinc salts therein. The precipitate is recovered by filtration, or centrifugation, and the mother liquors are discharged to an effluent treatment system.

The following examples are illustrative of the process of this invention. All parts are by weight unless otherwise indicated. All yields are based on the assumption that the 2,4,5,6-tetraaminopyrimidine sulfate is not hydrated.

EXAMPLE 1

To a reactor vessel equipped with an addition funnel, a mechanical stirrer, and a thermometer are charged one liter of water, 5-nitroso-2,4,6-triaminopyrimidine (91.1 grams of 90.5% real; 0.535 mole), and zinc dust (76.97 grams; 1.177 mole) to give a slurry having a temperature of 18°-19° C. and a pH of 10.1. To the stirred slurry is added dilute hydrochloric acid (375 mls of a solution of one part by volume of concentrated hydrochloric acid and one part by volume of water) over a period of 40 minutes, while allowing the temperature to rise to 60°-61° C., to give a reaction mixture having a pH of 5.6. Upon completion of the addition of the acid, the reaction mixture is stirred at 55°-65° C. for an additional 15-30 minutes and concentrated hydrochloric acid (53 mls) is then added to lower the pH to 2.2-2.3. Activated carbon (8.25 grams of Carbon Activated RB; Pittsburgh Coke & Chemical Co.) and a filter-aid (16.5 grams of Hyflo ® Super-Cel, Johns-Manville Corp.) are then added and the resulting mixture is stirred at 60°-65° C. for 15-20 minutes before filtering it through a steam-jacketed Büchner funnel. The filter cake is then washed with 100 mls of water at 60°-65° C. and the washing is combined with the filtrate. The combined liquors are then heated to 55°-60° C. and sulfuric acid (500 mls of 16.7% by weight) is added thereto at 50°-55° C. to obtain a pH of 0.5. The resulting slurry is cooled to 5°-10° C. over a period of about 75 minutes and maintained at 5°-10° C. for an additional 15-30 minutes. The reaction mixture is then filtered and the cake is washed with 500 mls of water at 5°-10° C. The washed cake is then dried at 60°-65° C. under a vacuum of 25-26 inches of mercury for 23 hours to obtain 108.55 grams of product which is 96.9 weight percent real by high-pressure liquid chromatography. The real yield of product is 82.5% of theoretical.

EXAMPLE 2

To a reactor vessel equipped with an addition funnel, a mechanical stirrer, and a thermometer are charged 2970 mls of water, and 5-nitroso-2,4,6-triaminopyrimidine (176.4 grams of 93.5% real; 1.07 moles). The mixture is heated to 45° C.±2° C. and the pH is adjusted to 5.5±0.2 by adding 5 mls of dilute hydrochloric acid, prepared by mixing 500 mls of concentrated hydrochloric acid and 500 mls of water. Zinc dust (175.4 grams; 2.7 moles) is added to the reaction mixture over a period of 30 minutes while adding the dilute hydrochloric acid to maintain the pH at 5.5±0.2. After the addition of the zinc dust is completed, the reaction mixture is stirred at 45° C.±2° C. for one hour while maintaining the pH at 5.5±0.2. A total of 696 mls of dilute hydrochloric acid is required to maintain the pH at 5.5 after the addition of the zinc dust is initiated. Concentrated hydrochloric acid (120 mls) is then added to lower the pH to 2.2-2.4. Activated carbon (16.5 grams of Carbon Activated RB) and a filter-aid (33 grams of Hyflo ® Super-Cel) are added to the solution and the resuulting mixture is filtered through a steam-jacketed Büchner funnel. The filter cake is then washed with 100 mls of water and the washing is combined with the filtrate. The combined liquors are then cooled below 40° C. and 16.7% sulfuric acid (625 mls) is added to lower the pH to 0.3. The resulting slurry is cooled to 0°-10° C., stirred for 30 minutes at 0°-10° C. and filtered. The filter cake is then washed with 1000 mls of water at 0°-5° C., sucked dry, and vacuum dried to obtain 246.1 grams of product which is 88.5% real by high-pressure liquid chromatography. The real yield is 85.5% of theoretical.

Having thus described the invention, what is claimed is:

1. A process for preparing 2,4,5,6-tetraaminopyrimidine sulfate (TAPS) comprising (1) reacting about one molecular proportion of 5-nitroso-2,4,6-triaminopyrimidine (NTAP) in water with about 2.0 to 2.5 molecular proportions of zinc dust and about 4.0 to 4.7 molecular proportions of a suitable acid to provide a reaction mixture having a pH below 7; (2) reacting said reaction mixture at a temperature of about 20° to 65° C. to form the acid salt of 2,4,5,6-tetraaminopyrimidine; (3) adjusting the pH to about 2.0 to 2.5 by adding said acid to form a solution of said salt; (4) separating the insoluble materials from step (3) to obtain a wet cake and a mother liquor; (5) adding sulfuric acid to said mother liquor to adjust the pH to about 0.2 to 0.5 while maintaining the temperature at about 20° to 60° C.; (6) cooling the reaction mixture of step (5) to about 0° to 10° C. the precipitate 2,4,5,6-tetraaminopyrimidine sulfate; and (7) recovering said precipitate.

2. The process of claim 1 wherein in step (1) said zinc dust is added and then said acid is added at a rate to provide a temperature rise of about 1° C. per minute and a final pH of about 5 to 6.

3. The process of claim 2 wherein in step (1) about 2.1 to 2.2 molecular proportions of zinc dust are added and then about 4.1 to 4.2 molecular proportions of hydrochloric acid are added, to provide a final temperature of about 50° to 65° C. and a final pH of about 5.5 to 5.7; in step (3) the pH is adjusted to about 2.2 to 2.4; and in step (5) about 15-20% by weight of sulfuric acid is added to adjust the pH to about 0.2 to 0.5 while maintaining the temperature at about 40° to 45° C.

4. The process of claim 1 wherein in step (1) said zinc dust and acid are added concurrently at a rate to provide a temperature rise of about 1° C. per minute and a final pH of about 5 to 6.

5. The process of claim 4 wherein in step (1) about 2.1 to 2.2 molecular proportions of zinc dust and about 4.1 to 4.2 molecular proportions of hydrochloric acid per molecular proportion of 5-nitroso-2,4,6-triaminopyrimidine are added concurrently at a rate to provide a final temperature of about 50° to 65° C. and a final pH of about 5.5 to 5.7; in step (3) the pH is adjusted to about 2.2 to 2.4; and in step (5) about 15 to 20% by weight of sulfuric acid is added to adjust the pH to about 0.2 to 0.5 while maintaining the temperature at about 40° to 45° C.

6. The process of claims 3 or 5 wherein said hydrochloric acid is a mixture of one part by volume of concentrated hydrochloric acid and one part by volume of water.

7. The process of claims 1 or 2 or 4 wherein said acid is selected from the group consisting of hydrochloric acid, hydrobromic acid, sulfuric acid, phosphoric acid, formic acid, acetic acid, and mixtures thereof.

* * * * *